United States Patent [19]

Bokros

[11] 4,169,477
[45] Oct. 2, 1979

[54] ANASTOMATIC COUPLINGS

[75] Inventor: Jack C. Bokros, Alpine, Calif.

[73] Assignee: CarboMedics, Inc., San Diego, Calif.

[21] Appl. No.: 813,538

[22] Filed: Jul. 7, 1977

[51] Int. Cl.$^2$ ............................................. A61B 17/11
[52] U.S. Cl. .................................. 128/334 R; 29/447; 285/381; 285/DIG. 10
[58] Field of Search ............... 128/1 R, 334 R, 334 C; 285/381, DIG. 10; 29/447

[56] References Cited

U.S. PATENT DOCUMENTS

| 3,315,986 | 4/1967 | Quick | 285/381 X |
| 3,357,432 | 12/1967 | Sparks | 128/334 C |
| 3,567,259 | 3/1971 | Benson et al. | 285/242 X |
| 3,781,969 | 1/1974 | Anderson | 29/447 X |

*Primary Examiner*—Dalton L. Truluck
*Attorney, Agent, or Firm*—Fitch, Even & Tabin

[57] ABSTRACT

A tubular vascular graft is attached to a rigid tubular portion of an implantable prosthetic device by assembling the vascular graft plus a surrounding heat-shrinkable polymeric sleeve on the rigid tubular portion. The polymeric sleeve, which may be TEFLON-FEP, extends a short distance past the free end of the tube and upon heating shrinks into firm compressive contact with the vascular graft and provides a smooth transition in stiffness between the end of the rigid tube and the soft, flexible graft.

10 Claims, 4 Drawing Figures

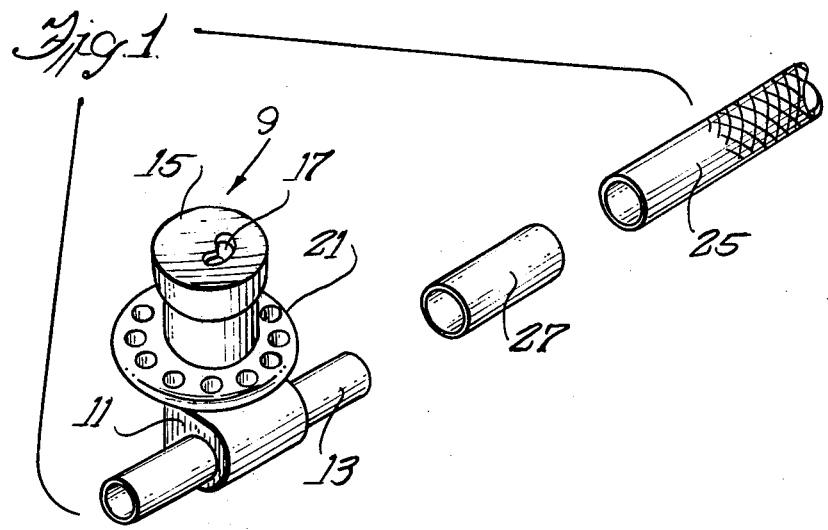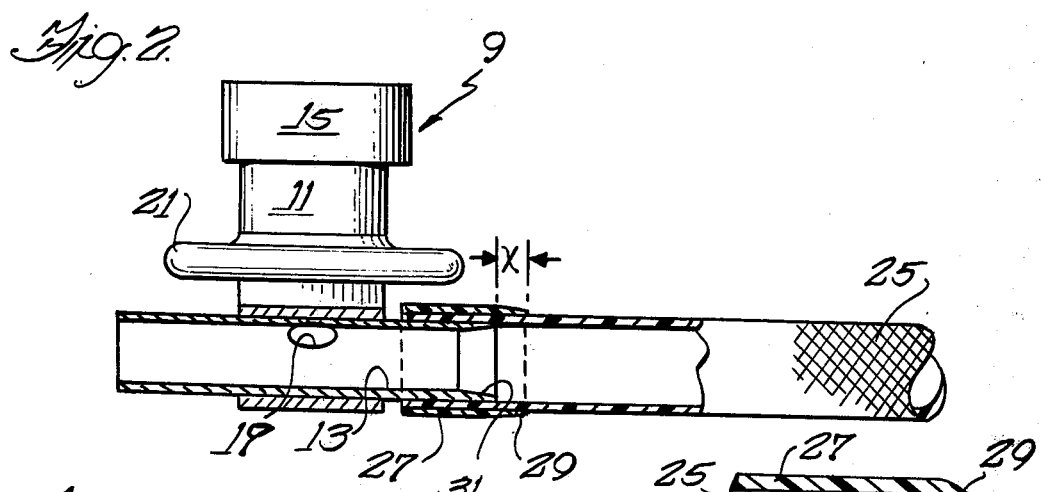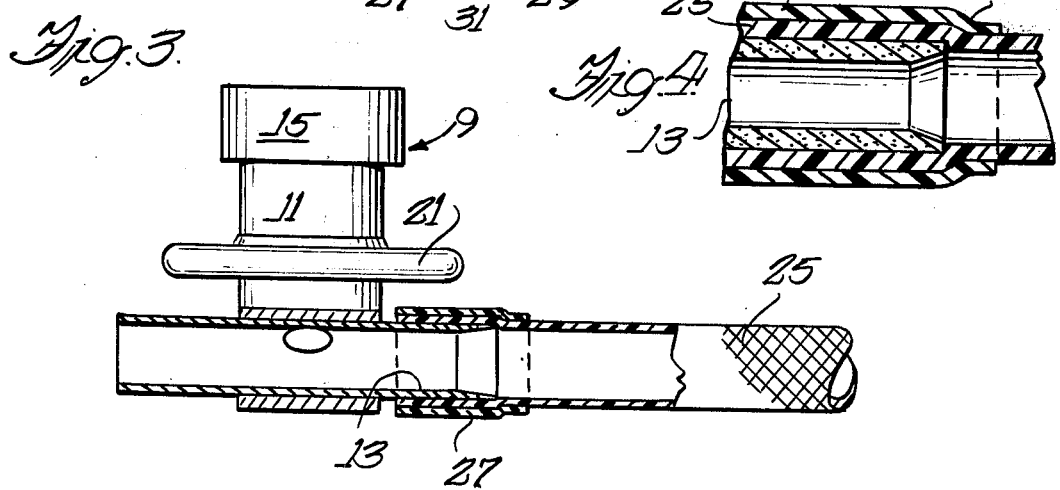

ANASTOMATIC COUPLINGS

This invention relates to anastomotic couplings and more particularly to a method for connecting a blood vessel graft to a rigid tube.

As science makes possible the substitution of artificial or prosthetic devices for parts of the human body, this area becomes of more and more interest to the medical community. Numerous types of surgical vascular prostheses have been developed as exemplified by U.S. Pat. Nos. 3,029,819 (Apr. 17, 1962), 3,588,920 (June 29, 1971) and 3,945,052 (Mar. 22, 1976). The broad method of repairing an intravascular defect within a human body by using a carbon-coated tubular device is taught in U.S. Pat. No. 3,526,005 to Bokros and Ellis.

In addition to simply repairing a vascular defect or the like, there have been recent advances where access devices of different types have been semipermanently implanted in the body in order to facilitate repeated entry to the bloodstream of a living person. For example, for the repeated withdrawing or injection of blood over a prolonged period. One illustrative device of this sort is shown in U.S. Pat. No. 4,015,601, issued to Bokros and Slivenko on Apr. 5, 1977. The preferred way of installing such a blood access device is to provide it with short vascular grafts which can be appropriately sutured to the circulatory system of the body. Various anastomotic couplings have been devised for joining a vascular graft to such a device, as exemplified by U.S. Pat. Nos. 3,155,095 (Nov. 3, 1964), 3,357,432 (Dec. 12, 1967) and 3,435,823 (Apr. 1, 1969); however, these coupling devices are in certain ways fairly complicated and not entirely satisfactory.

The present invention provides a simple and extremely effective method for joining a vascular graft to a prosthetic device. Heat-shrinkable polymeric tubing is used to its ultimate advantage in joining a vascular graft to a tubular portion of a prosthetic device.

Other objects and advantages of the invention will be apparent from the following detailed description of a preferred embodiment of the invention when read in conjunction with the accompanying drawings wherein:

FIG. 1 is an exploded perspective view illustrating representative components prior to their joinder;

FIG. 2 is an enlarged view partially in section showing the components illustrated in FIG. 1 in their assembled form;

FIG. 3 is a view similar to FIG. 2 showing the components after joinder has been effected; and FIG. 4 is a fragmentary view, enlarged in size, of a portion of FIG. 3.

Depicted in FIG. 1 is an implantable prosthetic device 9 in the form of a blood access device which includes a main housing portion 11 and a rigid tubular portion 13 near the lower end thereof of the appropriate size and shape for interconnection into the body's circulatory system. The upper end of the housing 11 is threaded and receives a cap 15 which has an opening 17 that provides access to a rotatable valve member carried in the housing 11 that has a passageway which extends downward therethrough and, when in the open position, registers with a hole 19 in the tubular portion 13 that will be joined to the circulatory system. The housing 11 also includes a radially extending apertured collar 21 which stabilizes the implantation of the device 9 in the human body and provides a structure into which body tissue will grow.

The tubular connecting portion 13 is preferably a tube made of nonthrombogenic carbon, as by the method described in U.S. Pat. No. 3,399,969 and available from General Atomic's Medical Products Division under the trademark PYROLITE. Alternatively, a suitable substrate may be coated with nonthrombogenic carbon as described in U.S. Pat. No. 3,526,005. Such carbon renders the tubular connecting portion 13 fully compatible with blood and is an effective guard against clotting which is a distinct concern whenever artificial materials are exposed to the human bloodstream.

The tubular portion 13 of the prosthetic device is connected at each end to a short vascular graft 25 by a heat-shrinkable polymeric sleeve 27. The vascular graft may be made in any suitable manner, such as those described in the aforementioned U.S. patents. For example, it may be woven of a suitable synthetic fiber. The heat-shrinkable sleeve 27 should be of a material which will be compatible with body tissue, and heat-shrinkable fluorocarbons are preferred. One example is a copolymer of tetrafluroethylene and hexafluoropropylene which is marketed by DuPont under the trademark TEFLON-FEP and is considered excellent because of its chemical inertness when exposed to body tissue and fluids. Heat-shrinkable tubing is generally produced by extrusion, followed by expansion in a radial direction and by cooling in the expanded condition, and tubing of TEFLON-FEP is commercially available which will shrink upon heating to a temperature of about 300° F. The diameter of the sleeve 27 in both its expanded and its unexpanded forms is important as discussed hereinafter.

As apparent from FIG. 2, the tubular vascular graft 25 should have an inner diameter which is approximately equal to the outer diameter of the rigid tubular portion 13 so that it can be snugly accommodated thereon. The heat-shrinkable polymeric sleeve 27, in its expanded form, is sized to have an inner diameter slightly larger than the outer diameter of the vascular graft 25. A sleeve of sufficient length is used so that, when positioned over the assembled prosthetic device 9 and graft 25, it extends for a short distance past the free end of the rigid tubular portion 13, which distance is depicted by the reference letter X in FIG. 2. Preferably, this distance X is equal to at least about 10 percent of the outer diameter of the tubular portion and not greater than about 50 percent. The sleeve 27 is preferably formed with a taper 29 for at least the distance X by suitably shaving away or feathering the exterior surface thereof for a purpose explained hereinafter. To facilitate its machining, if necessary, the temperature of the polymeric sleeve may be lowered to rigidify it.

Upon heating to a temperature of about 300° F., the exterior polymeric sleeve promptly shrinks to press the vascular graft 25 into firm contact against the outer surface of the tubular portion 13 of the prosthetic device as a result of trying to return to its original unexpanded form. At the region immediately past the free end of the tubular portion 13, as best seen in FIG. 4, the shrunken sleeve 27 compresses the vascular graft in a radial direction, forcing it inward so that the inner surface of the vascular graft 25 is substantially aligned with the inner surface of the tubular portion. To achieve this function, the sleeve 27 should have a length at least equal to the tube outer diameter and should have an unexpanded inner diameter slightly less than the outer diameter of the vascular graft 25. Because of the tapered configuration of the polymeric sleeve 27, the rigidity of the support it provides the graft will vary along the length of the tapered portion. As a result, a desirable smooth transition in stiffness is achieved from the rigid tube to the soft, flexible graft. To avoid over-compressing the vascular graft, the unexpanded inner diameter should not be less than about 85 percent of the outer diameter of the vascular graft. The interior surface of the end of the tubular portion 13 is also formed with a slightly outward taper 31 to further assure a smooth transition at this important location.

The precision of matching the interior diameters at this point is of importance because, if there is any gap, the formation of a culdesac at this point becomes a distinct possibility, and the likelihood of such formation is indeed heightened by the fact that the pulsing of blood through the circulatory system, as the heart beats, has the natural tendency to expand the vascular graft outward at this point. However, the shrunken polymeric sleeve 27 excellently maintains the illustrated configuration over a long period of time because it continues to slightly compress the vascular graft and thus provides a tight connection at the end edge of the tubular portion 13 of the prosthetic device. Because the sleeve maintains at this point and because the feathered edge assures a smooth transition in stiffness, the formation of a culdesac is effectively eliminated.

As one example of a coupling embodying features of the invention, a blood access device 9 of the type depicted in FIG. 1 may be manufactured having a tubular portion 13 which is about 2 centimeters long. The tube 13 is made of solid PYROLITE carbon, and the outer diameter of the tube is about 6 mm. The wall thickness of the tube is about 0.5 mm. and there is a slight outward taper in the interior surface of the tube 13 extending for a distance about 1 mm from each free end. The vascular graft 25 is formed of closely woven tubing, appropriately treated, which has an inner diameter equal to the outer diameter of the tube 13 and a wall thickness of about 0.5 mm. The heat-shrinkable sleeve 27 is made from TEFLON-FEP having a wall thickness of about 0.5 mm and an expanded interior diameter of about 9 mm. The original diameter of the extruded sleeve (i.e., the unexpanded diameter) was about 6.5 mm, and it will attempt to return to this inner diameter upon heating to a temperature of about 300° F. The sleeve 27 is about 1 cm long and is positioned so that the distance X (FIG. 2) is about 1 mm, and its overhanging portion is feathered so that the wall thickness at the end of the sleeve is about one-half of the nominal thickness. The heat-shrunk sleeve 27 firmly unites the graft to the tube 13 and compresses it to provide a smooth transition at the end edge of the tube while also providing a smooth transition in stiffness, from rigid to flexible.

Although the illustrated method of assembly is eminently simple, it creates a coupling that is compatible with body tissue and which is clearly simpler than earlier couplings. The illustrated blood access device 9 might be connected to a small artery, either in the artery itself or parallel thereto, or it could be located as a shunt between an artery and a vein. The prosthetic device could take a variety of shapes; for example, it might be a simple T-shaped tap. Even more simply, it could be a simple tube to repair a defective arterial section. Moreover, a tube of a diameter small enough to fit into a blood vessel might be used with the tubular graft extending past the adjacent end of the shrunken sleeve so it can be sutured to the vessel after insertion.

Although the invention has been illustrated and described with respect to certain preferred embodiments, it should be understood that changes and modifications can be made such as would be obvious to one having the ordinary skill in the art without departing from the scope of the invention which is defined solely by the claims appended hereto. Various of the features of the invention are set forth in the claims which follow.

What is claimed is:

1. A method of attaching a vascular graft to an implantable prosthetic device including a rigid tubular portion, which method comprises
    providing a tubular vascular graft having an inner diameter approximately equal to the outer diameter of the rigid tubular portion,
    providing a heat-shrinkable polymeric sleeve having an inner diameter at least equal to the outer diameter of the vascular graft and having an end portion which tapers to a substantially smaller wall thickness,
    assembling the vascular graft on the rigid tubular portion with said polymeric sleeve disposed in surrounding relation to the portion of the graft in contact with the tubular portion and said tapering end portion extending for a distance past the free end of said tubular portion and
    heating said assembly to shrink the sleeve into firm compressive contact with the vascular graft so that the portion of the graft just adjacent the end of the tubular portion is compressed and firmly supported by said shrunken sleeve whereby there is a smooth transition in stiffness that eliminates formation of a culdesac.

2. A method in accordance with claim 1 wherein said sleeve tapered end extends past the free end a distance at least equal to about 10 percent the outer diameter of the tubular portion.

3. A method in accordance with claim 1 wherein said heat-shrinkable sleeve is made of a flurocarbon polymer.

4. A method in accordance with claim 2 wherein said heat-shrinkable sleeve is a copolymer of tetrafluoroethylene and hexafluoropropylene.

5. A method in accordance with claim 4 wherein said heat-shrinking is effected by raising the temperature of the sleeve to between about 250° F. and 350° F.

6. An anastomatic coupling for joining a vascular graft to an implantable prosthetic device having a rigid tubular portion, which coupling comprises
    a tubular vascular graft disposed upon a rigid tubular portion of the prosthetic device and extending well past the free end thereof for suturing to a blood vessel, said tubular graft having an inner diameter approximately equal to the outer diameter of the tubular portion, and
    a heat-shrunk polymeric sleeve, having an unexpanded inner diameter slightly less than the outer diameter of said vascular graft and having an end portion which tapers to a substantially smaller wall thickness, disposed in surrounding compressive relation to the portion of said graft in contact with the tubular portion and with said tapered end portion extending for a substantial distance past the free end thereof, said shrunken sleeve holding said vascular graft in firm contact with the tubular portion and the extended part of said shrunken sleeve compressing said graft in the region adjacent the end of said tubular portion and thus providing a smooth internal transition adjacent the end edge of the tube and a smooth transition in stiffness that eliminates formation of a culdesac.

7. A coupling in accordance with claim 6 wherein said heat-shrinkable sleeve is a flurocarbon.

8. A coupling in accordance with claim 6 wherein said sleeve tapered end extends past said free end of said tubular portion a distance at least equal to about 10 percent of the outer diameter of said tubular portion.

9. A coupling in accordance with claim 8 wherein said heat-shrunk sleeve is a copolymer of tetrafluoroethylene and hexafluoropropylene and tapers to a lesser wall thickness which is not greater than about one-half of the nominal wall thickness of said sleeve.

10. A coupling in accordance with claim 6 wherein said tubular portion comprises biocompatible carbon and has an interior surface that is formed with an outward taper.

* * * * *